United States Patent
Felix et al.

(10) Patent No.: US 6,518,442 B1
(45) Date of Patent: Feb. 11, 2003

(54) PROCESS FOR THE RECOVERY OF FLUORINATED ALKANDIC ACIDS FROM WASTEWATER

(75) Inventors: Bernd Felix, Burgkirchen (DE); Tilman Zipplies, Burghausen (DE); Stephan Führer, Burgkirchen (DE); Thomas Kaiser, Kelkheim (DE); Armin Budesheim, Wiesbaden-Naurod (DE)

(73) Assignees: Dyneon GmbH & Co., KG (DE); Axiva GmbH (DE)

( * ) Notice: Subject to any disclaimer, the term of this patent is extended or adjusted under 35 U.S.C. 154(b) by 0 days.

(21) Appl. No.: 09/700,639

(22) PCT Filed: May 27, 1999

(86) PCT No.: PCT/EP99/03673

§ 371 (c)(1),
(2), (4) Date: Nov. 16, 2000

(87) PCT Pub. No.: WO99/62830

PCT Pub. Date: Dec. 9, 1999

(30) Foreign Application Priority Data

Jun. 2, 1998 (DE) .......... 198 24 615

(51) Int. Cl.⁷ .......... C07C 51/43; C07C 53/21; C07C 51/42

(52) U.S. Cl. .......... 554/177; 562/605; 562/608; 252/302; 252/315.4; 510/315.1

(58) Field of Search .......... 554/177; 562/605, 562/608; 252/302, 315.4; 510/315.1

(56) References Cited

U.S. PATENT DOCUMENTS

| | | | | |
|---|---|---|---|---|
| 3,882,153 A | | 5/1975 | Seki et al. | 260/408 |
| 4,282,162 A | | 8/1981 | Kuhls | 260/408 |
| 4,369,266 A | * | 1/1983 | Jurgen et al. | |
| 5,312,935 A | | 5/1994 | Mayer et al. | 554/182 |
| 5,442,097 A | | 8/1995 | Obermeier et al. | 560/227 |

FOREIGN PATENT DOCUMENTS

| | | | |
|---|---|---|---|
| DE | A 20 44 986 | 9/1970 | |
| EP | A 566 974 | 4/1993 | C07C/53/21 |

* cited by examiner

*Primary Examiner*—Jafar Parsa
(74) *Attorney, Agent, or Firm*—James V. Lilly; Brian E. Szymanski

(57) ABSTRACT

The invention relates to a method for removing fluorinated emulsifying agent acids from waste waters, characterized in that the finely dispersed solids in the waste water are stabilized with a nonionic or cationic surfactant or an analogous acting surface active substance, the fluorinated emulsifying agent acids are subsequently bonded on an anion exchange resin and the fluorinated emulsifying agent acids are eluted from the latter.

6 Claims, No Drawings

PROCESS FOR THE RECOVERY OF FLUORINATED ALKANDIC ACIDS FROM WASTEWATER

This application is a 371 of PCT/EP 99/03673 filed May 27, 1999.

In the polymerization of fluorinated monomers in aqueous dispersion, use is made of fluorinated alkanoic acids as emulsifiers since they have no telogenic properties. In particular, use is made of the salts, preferably the alkali metal or ammonium salts, of perfluorinated or partially fluorinated alkane-carboxylic acids or alkane-sulfonic acids. These compounds are prepared by electrofluorination or by telomerization of fluorinated monomers, which is costly. There have therefore been many attempts to recover these valuable materials from wastewater.

U.S. Pat. No. 5,442,097 discloses a process for the recovery of fluorinated carboxylic acids in usable form from contaminated starting materials. In this process, the fluorinated carboxylic acid is, if necessary, liberated from these materials in an aqueous medium using a sufficiently strong acid, the fluorinated carboxylic acid is reacted with a suitable alcohol and the ester formed is distilled off. The starting material can here be a polymerization liquor, in particular from an emulsion polymerization in which the fluoropolymer is prepared in the form of colloidal particles with the aid of relatively high amounts of emulsifier. This process has proven very useful, but requires a certain concentration of fluorinated carboxylic acid in the starting material. DE-A-20 44 986 discloses a process for the recovery of perfluorocarboxylic acids from dilute solution, in which the dilute solution of the perfluorocarboxylic acids is brought into adsorption contact with a weak base anion-exchange resin and the perfluorocarboxylic acid present in the solution is thereby adsorbed on the anion-exchange resin, the anion-exchange resin is eluted with an aqueous ammonia solution and the adsorbed perfluorocarboxylic acid is thus transferred into the eluant and the acid is finally isolated from the eluate. However, complete elution requires relatively large amounts of dilute ammonia solution and this process is also very time-consuming. These disadvantages are overcome by the process known from U.S. Pat. No. 4,282,162 for the elution of fluorinated emulsifier acids adsorbed on basic anion exchangers, in which the elution of the adsorbed fluorinated emulsifier acid from the anion exchanger is carried out using a mixture of dilute mineral acid and an organic solvent. In this process, the ion-exchange resin is regenerated at the same time by use of the acid.

It has been found that this last-named process presents problems in industrial practice when, in particular, the wastewater processed contains very fine solids which in the past were often not recognized or at least not recognized as causing a problem. In this case, the apparatuses containing the anion-exchange resin become clogged with these solids more or less quickly, which becomes noticeable as a result of increased flow resistance and reduced performance. The upstream filters or frits customarily used are ineffective here.

It has also been found that these difficulties are caused by the fine solids being trapped in relatively stable colloidal suspension by the emulsifier acids. When these acids are then removed from the system by means of the anion-exchange resin, this relatively stable dispersion is destroyed and the solid is precipitated and clogs the ion-exchange resin. It was thus also found that the performance of the process known from U.S. Pat. No. 4,282,162 can be considerably improved and also made suitable for wastewater containing fine solids if the dispersion of the solids in the wastewater is stabilized by addition of a nonionic or cationic surface-active additive (surfactant) before the wastewater is brought into contact with the anion exchanger. The nonionic or cationic surfactants are not bound by the anion exchanger.

The invention accordingly provides a process for the recovery of fluorinated emulsifier acids from wastewater, which comprises stabilizing the solids which are finely dispersed in the wastewater by means of a nonionic or cationic surfactant or a surface-active substance having an analogous effect and subsequently binding the fluorinated emulsifier acids to an anion-exchange resin and eluting the fluorinated emulsifier acids from this.

Wastewater suitable for treatment is waste process water in which surface-active fluorinated alkanoic acids are present. The process is particularly suitable for wastewater from the polymerization of fluorinated monomers by the emulsion method, in which the fluorinated monomer is converted in the presence of a relatively high concentration of fluorinated emulsifier acid and with mild stirring into a finely divided polymer which is in finely dispersed, colloidal form and in which the latex obtained is coagulated, for example by intensive stirring, after the desired solids concentration has been reached, so that the polymer precipitates as a fine powder.

It has been found that in the known work-up it is especially relatively low molecular weight polymer material which causes difficulties; the adverse effect of these low molecular weight polymers becomes particularly noticeable when the polymerization process leads to a broad molecular weight distribution. In the case of such "difficult" wastewater too, the process of the invention displays its capabilities.

The removal of solids before the wastewater is brought into contact with the ion-exchange resin is also known (German patent application 198 24 614.5 of Jun. 2, 1998 with the title "Verfahren zur Rückgewinnung von fluorierten Alkansäuren aus Abwässern"). However, this has the disadvantage of a high outlay in terms of apparatus for the solids removal and the amount of auxiliary chemicals to be added (for example milk of lime, aluminum salts, flocculants). Particularly at low solids concentrations, complete removal of the colloidal material requires relatively large amounts of chemicals which are removed again to only a limited extent in the solids removal.

In the process of the invention, the outlay in terms of apparatuses and chemicals is considerably reduced since the addition of small amounts of a preferably readily biodegradable surfactant is sufficient for stabilizing the colloids and ensures trouble-free operation of the ion exchanger.

The adsorption of the emulsifier acids onto ion-exchange resins can be carried out in a manner known per se. Suitable resins are, in particular, strong base anion-exchange resins as are obtainable, for example, under the trade names ®AMBERLITE IRA-402, ®AMBERJET 4200 (both Rohm & Haas), ®PUROLITE A845 (Purolite GmbH) or ®LEWATIT MP-500 (Bayer AG).

The adsorption can be carried out in a manner known per se, with the ion-exchange resins being located in customary apparatuses such as tubes or columns through which the wastewater flows.

The elution of the bound emulsifier acids is likewise carried out in a manner known per se, with preference being given to the method described in U.S. Pat. No. 4,282,162.

Methods suitable for isolating the emulsifier acids in the high purity required for use in polymerization are, for example, those described in the abovementioned U.S. Pat. No. 5,442,097 or that described in U.S. Pat. No. 5,312,935 in which the eluate is firstly substantially freed of water and then treated with oxidizing agents.

The wastewater remaining after adsorption of the emulsifier acids is treated in a known manner, depending on the content of other materials.

The invention is illustrated by the following examples.

EXAMPLES 1 TO 4 AND COMPARATIVE EXAMPLE

The starting material used is wastewater from the copolymerization of tetrafluoroethylene and perfluoro(n-propyl vinyl ether) in which the ammonium salt of n- and iso-perfluorooctanoic acid (PFOA) is used as emulsifier. The PFOA concentration is 750 mg/l.

In a stirred vessel, 1000 g of this liquor are admixed with 0.1 g of the nonionic surfactant ®TRITON X-100 (Rohm & Haas, p-octylphenol ethoxylate, CAS No. 9002-93-1) or ®GENAPOL UD 088 (Hoechst AG, fatty alcohol polyglycol ether) and stirred.

About 50 ml of a commercial strong base ion-exchange resin (®AMBERLITE IRA-402, Rohm & Haas; styrene-divinylbenzene type, anion: chloride, gel, total capacity: 1.3 eq/l, bulk density: 710 g/l) are placed in a cylindrical glass column (length: 25 cm, diameter: 16 mm) provided with a glass frit and rinsed with water. To load the ion exchanger, the solution is pumped upward through the bed by means of a pump. The water leaving the column is collected as a plurality of samples and the PFOA concentration is determined. The pressure drop over the ion exchanger bed is measured by means of a manometer. The water leaving the column is collected as a plurality of samples and the PFOA concentration is determined.

The loading experiment without addition of surfactant (comparative example) had to be stopped since the pressure drop increased to above 1 bar/m as a result of precipitated polymer and the resin displayed significant conglutination.

|  | Surfactant: Concentration | Example 1 | Example 2 | Example 3 | Example 4 | Comparative Example |
|---|---|---|---|---|---|---|
| Amount of wastewater [ml] |  | ® GENAPOL 100 mg/l | ® TRITON 100 mg/l | ® TRITON 200 mg/l | ® TRITON 400 mg/l | none |
| Pressure drop over ion exchanger bed [bar/m] ||||||||
| 0 |  | 0.12 | 0.24 | 0.24 | 0.16 | 0.20 |
| 200 |  | 0.16 | 0.20 | 0.24 | 0.16 | 0.40 |
| 300 |  | 0.12 | 0.24 | 0.24 | 0.24 |  |
| 400 |  | 0.12 | 0.24 | 0.24 |  | 1.60 (stopped) |
| 500 |  | 0.12 | 0.24 |  | 0.24 |  |
| 600 |  | 0.12 | 0.24 |  | 0.24 |  |

-continued

|  | Example 1 | Example 2 | Example 3 | Example 4 | Comparative Example |
|---|---|---|---|---|---|
| 1000 | 0.12 |  |  |  |  |
| PFOA in the wastewater mg/l | 2.5 | 5.1 | 4.2 | 4.2 | 3.3 |

EXAMPLE 5

150 ml of an elution solution are mixed from methanol, concentrated sulfuric acid (96%) and water (proportions by mass: 89%, 7%, 4%). The ion exchanger column is, after loading, firstly rinsed with 100 ml of water in order to remove remaining wastewater from the column. The elution solution is then passed through the column at a linear velocity of 0.5 m/h and is collected. The column is finally rinsed with a further 50 ml of water. The elution solution contains about 95% of the emulsifier solution in the wastewater used.

What is claimed is:

1. A process for the removal of fluorinated emulsifier acids and salts thereof from a wastewater stream that originates from the making of fluoropolymers, which wastewater stream contains finely divided fluoropolymer solids, the process comprising a) adding a non-ionic or cationic surfactant to the wastewater stream to stabilize the finely dispersed polymer solids and subsequently b) contacting the wastewater stream with an anion exchange resin to bind the fluorinated emulsifier acids and salts to the anion exchange resin.

2. The process according to claim 1 comprising precipitating the finely dispersed fluoropolymer solids after they have been stabilized by the non-ionic surfactant.

3. The process according to claim 1 wherein the anion exchange resin used in step b) is a strong base anion exchange resin.

4. The process according to claim 1 comprising eluting the fluorinated emulsifier acids and salts from the anion exchange resin.

5. The process according to claim 4 wherein elution is carried out using a mixture of dilute mineral acid and an organic solvent.

6. The process according to claim 1 wherein the amount of non-ionic surfactant used in step a) is 400 mg/l or less.

* * * * *

UNITED STATES PATENT AND TRADEMARK OFFICE
CERTIFICATE OF CORRECTION

PATENT NO. : 6,518,442 B1
DATED : February 11, 2003
INVENTOR(S) : Felix, Bernd

It is certified that error appears in the above-identified patent and that said Letters Patent is hereby corrected as shown below:

Title page,
Item [54], Title, delete "PROCESS FOR THE RECOVERY OF FLUORINATED ALKANDIC ACIDS FROM WASTEWATER" and insert -- PROCESS FOR THE RECOVERY OF FLUORINATED ALKANOIC ACIDS FROM WATSEWATER --
Item [57], ABSTRACT,
1st line, delete "removing" and insert -- recovering --.

Column 1,
Line 29, "DE-A-20 44 986......." should be shown as the start of a new paragraph.

Signed and Sealed this

Thirteenth Day of July, 2004

JON W. DUDAS
*Acting Director of the United States Patent and Trademark Office*